United States Patent [19]

Blakeney

[11] Patent Number: 5,043,704
[45] Date of Patent: Aug. 27, 1991

[54] ENURESIS AVOIDANCE TRAINING AID

[76] Inventor: William D. Blakeney, 41135 W. Honeycutt Rd., Maricopa, Ariz. 85239

[21] Appl. No.: 491,723

[22] Filed: Mar. 12, 1990

[51] Int. Cl.$^5$ ............................................. G08B 21/00
[52] U.S. Cl. .................................. 340/573; 128/880; 200/61.05; 340/388; 340/604; 340/691
[58] Field of Search ............... 340/573, 604, 388, 691; 200/61.05; 128/886

[56]  References Cited

U.S. PATENT DOCUMENTS 3,441,019  4/1969  Kilgore .............................. 340/604
3,448,447  6/1969  Tetherow ........................... 340/691

Primary Examiner—Glen R. Swann, III
Attorney, Agent, or Firm—Lowell W. Gresham; Don J. Flickinger; Jordan M. Meschkow

[57] ABSTRACT

An apparatus which is worn to condition the wearer against bed wetting is disclosed. The apparatus includes a wetness sensor that has a circuit pattern in which a multiplicity of interleaved, spaced apart conductive fingers reside on a non-conductive substrate. The circuit pattern is optimized to quickly and reliably detect small quantities of urine. The substrate is curved into a three dimensional, cup-like shape which has an edge that conforms to the urogenital area of the wearer. A foam pad is positioned at this edge to help seal the wetness sensor against the wearer and to make the wetness sensor comfortable to wear. Electrical components couple to the wetness sensor and drive a speaker. The electrical components include a battery and a relay. The realy is configured to oscillate when the wetness sensor detects urine, and the oscillating relay causes the speaker to broadcast an alarm signal.

19 Claims, 1 Drawing Sheet

ENURESIS AVOIDANCE TRAINING AID

TECHNICAL FIELD OF THE INVENTION

The present invention relates generally to urine detection devices and methods. More specifically, the present invention relates to devices and methods which are useful in training a wearer to avoid enuresis.

BACKGROUND OF THE INVENTION

Enuresis, also called bet wetting or incontinence of urine during sleep, represents a serious problem to those who are afflicted. The extreme embarrassment which this condition forces upon the afflicted extracts a tremendous toll in self-esteem and psychological well-being. Moreover, the ruination of clothes and bedding, the cleaning chores, and the unsanitary conditions imposed by exposure to urine extract additional unwanted costs from those associated with a person afflicted with enuresis. Accordingly, a strong need exists for devices and techniques which help the afflicted overcome the condition.

Various training aids directed to the enuresis condition are known. Generally speaking, such training aids include an electrical sensing device which detects the presence of urine and is worn or otherwise located near the urethra. An electrical circuit sounds an alarm when the sensing device encounters urine. The alarm wakes the wearer. In theory, after continued use of such training aids, the wearer is conditioned to become consciously aware of his or her need to urinate, and wakes-up when this need arises.

While numerous versions of the above-described training aids are known, none have achieved wide acceptance because they suffer from various problems. For example, conventional enuresis training aids tend to be too costly for the average consumer. The excessive cost results, at least in part, from complex urine sensors, complex electrical circuits, or a requirement for disposable components which are not readily available. In addition, conventional enuresis training aids are often difficult to clean, uncomfortable for the wearer, and fail to prevent clothes from becoming soaked with urine. Consequently, such aids do not particularly motivate the wearer to continuously and faithfully use the aids. When the wearer fails to continuously and faithfully use the aid, the chances for becoming successfully conditioned to wake up when the need to urinate arises diminish.

Moreover, conventional enuresis training aids work unreliably or are otherwise too slow in sounding an alarm. These problems originate, in large part, from urine sensor designs. One type of conventional urine sensor requires a urine-absorbing material to absorb urine before an alarm sounds. For example, such a material may be sandwiched between two conductive screens. Alternatively, such a material may overlie two conductors which are spaced apart on a common surface. Such designs rely on capillary action to wick the urine into proximity with spaced apart conductors so that the electrolytic property of urine will form an electrical circuit between the spaced apart conductors. However, the use of an absorbing material results in a large quantity of urine being discharged before an alarm sounds.

As a result, the wearer does not wake up until the urination process is well under way. Consequently, such designs are not as effective in conditioning the wearer as they would be if the alarms sounded earlier. In addition, the absorbing materials are often particularly difficult to clean, which motivates against continuous and faithful use of the enuresis training aid. Furthermore, other conventional enuresis training aids attempt to ameliorate the reliability and speed of detection problems by tightly clamping the urine sensors to the wearer's urethra. Unfortunately, such tight clamping causes discomfort for the wearer, which again motivates against continuous and faithful use of the training aid.

SUMMARY OF THE INVENTION

Accordingly, it is an advantage of the present invention that an improved enuresis avoidance training aid is provided.

Another advantage of the present invention is that an improved enuresis training aid which tends to prevent clothing and bedding from becoming soaked with urine is provided.

Yet another advantage is that the present invention provides an improved enuresis training aid which is easily cleaned.

Still another advantage is that the present invention provides an improved enuresis training aid which quickly and reliably detects the presence of urine.

Another advantage is that the present invention provides an improved enuresis training aid which is comfortable for the wearer.

Yet another advantage is that the present invention provides an improved enuresis training aid which is inexpensive to purchase and use.

The above and other advantages of the present invention are carried out in one form by an apparatus which detects urine discharged from a body of a wearer. The apparatus includes a wetness sensor and a sound producing device. The wetness sensor includes a non-conductive substrate, which is configured to extend in each of three dimensions so that it forms a cup-like shape. The substrate is further configured so that it is sealable against the wearer's body. Thus, the urine is substantially retainable between the substrate and the wearer's body. The substrate additionally has an interior surface upon which a circuit pattern is formed. The circuit pattern includes two sets of interleaved, conductive fingers. When the wetness sensor detects the urine, the sound producing device emits an audible signal.

BRIEF DESCRIPTION OF THE DRAWINGS

A more complete understanding of the present invention may be derived by referring to the detailed description and claims when considered in connection with the FIGURES, wherein like reference numbers refer to similar items throughout the FIGURES, and:

DETAILED DESCRIPTION OF THE PREFERRED EMBODIMENT

Figure 1:
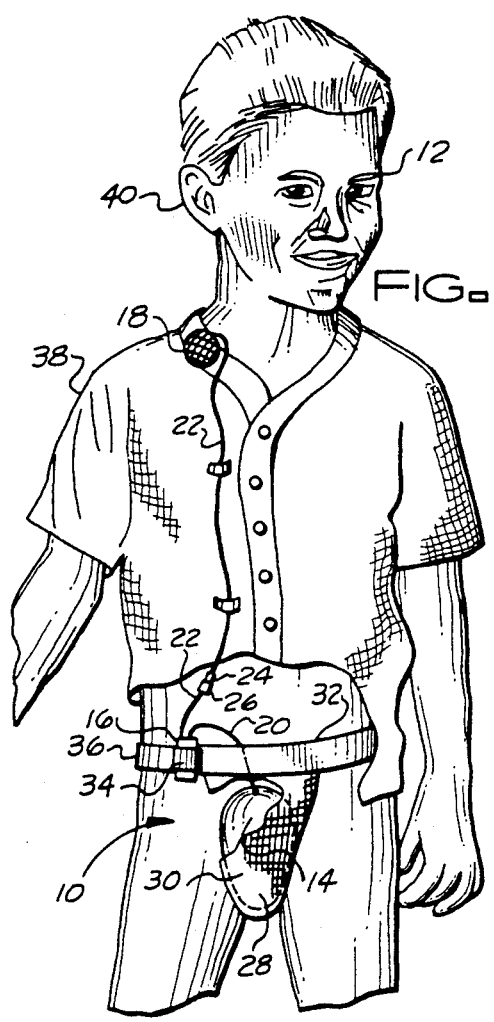
FIG. 1 shows a enuresis avoidance training aid constructed in accordance with the teaching of the present invention and installed on the body of a wearer.

FIG. 1 shows a enuresis avoidance training aid 10 being worn by a male wearer 12. Training aid 10 includes a wetness sensor 14, specifically shown in FIG. 3, electrical components 16, a speaker 18, and two-wire electrical cables 20 and 22. In addition, mating plug and socket connectors 24 and 26 are installed in cable 22.

In the preferred embodiment, wetness sensor 14 snugly fits against urogenital area 28 of wearer 12. Sensor 14 is held in place by being located within a cup 30 of a conventional athletic supporter 32. Alternately, sensor 14 may be located within conventional brief-type undergarments (not shown). Electrical cable 20 couples sensor 14 to components 16. In the preferred embodiment, components 16 are retained within an elastic pouch 34, which is pinned or otherwise removably fastened to an outside surface of a belt portion 36 of athletic supporter 32.

Cable 22 couples components 16 to speaker 18 and may be routed to speaker 18 using any convenient technique. To promote the comfort of wearer 12, cable 22 may be routed outside of a shirt 38, such as a pajama shirt. In addition, cable 22 may be taped or otherwise fastened to shirt 38 so that cable 22 tends not to become tangled or to cause interference with the sleep of wearer 12.

Speaker 18 is a relatively small audio loudspeaker which is pinned or otherwise removably fastened to the upper portion of shirt 38. Preferably, speaker 18 is oriented and fastened to shirt 38 so that its direction of audio propagation points generally toward an ear 40 of wearer 12. The preferred embodiment utilizes a model MOR-006L speaker manufactured by the Sony Corporation. This particular speaker is desirable due to its small diameter (approximately 1¼ inches), its high efficiency, and its small weight. The small size and light weight enhance the comfort of wearer 12, and the high efficiency permits an alarm sound emitted from speaker 18 to be relatively loud. However, those skilled in the art can easily adapt other speakers for use in connection with the present invention.

Generally speaking, training aid 10 is worn by wearer 12 while sleeping. Aid 10 wakes wearer 12 when wearer 12 begins to urinate. Wetness sensor 14 instantly detects the presence of urine, as discussed below in connection with FIGS. 3 and 4. Moreover, sensor 14 is physically configured to promote the comfort of wearer 12 and to be sealed against urogenital area 28 when worn by wearer 12 so that the urine is retained between area 28 and sensor 14. Electrical components 16, in cooperation with wetness sensor 14, produce an alarm signal, as discussed below in connection with FIG. 2, which speaker 18 audibly broadcasts. The alarm signal is sufficiently loud to wake wearer 12.

Once the alarm signal sounds, it continues until wearer 12 becomes sufficiently conscious to undertake an action to stop the alarm signal. Preferably, wearer 12 becomes totally conscious before the alarm signal may be stopped. Thus, wearer 12 becomes consciously aware of the need to urinate and can then urinate in the proper facilities. In accordance with this need to bring wearer 12 to total consciousness before an alarm signal may stop, the stopping of the alarm signal is relatively difficult compared, for example, to the simple deactivation of a switch. Specifically, wearer 12 must disconnect mating connectors 24 and 26 before the alarm signal stops. Preferably, connectors 24 and 26 may be separated only after wearer 12 exerts a relatively large pulling-apart force on connectors 24 and 26. This act requires both the exertion of preferably a few pounds of force and the coordinated activity of both of the wearer's hands. Accordingly, wearer 12 is forced to consciousness in order to stop the alarm.

Figure 2:
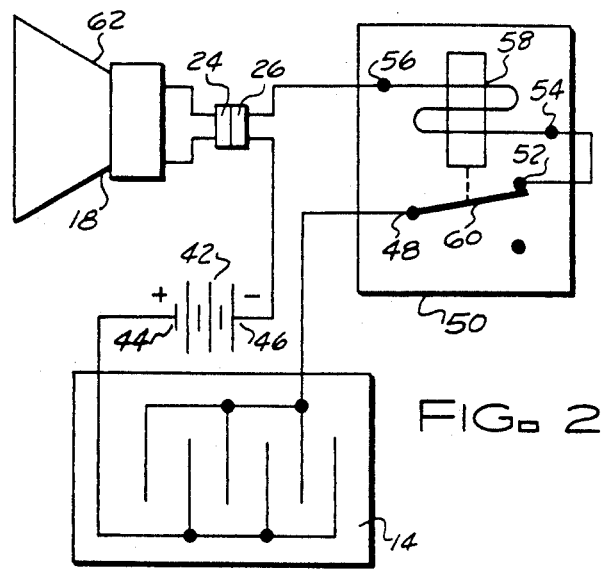
FIG. 2 shows a schematic diagram of the electrical circuit utilized by the present invention.

FIG. 2 shows a schematic diagram of the circuits employed by training aid 10. Specifically, aid 10 includes a battery 42, in which a positive terminal 44 couples to a first node of wetness sensor 14 and a negative terminal 46 couples to a first node of speaker 18 through connectors 24-26. A second node of wetness sensor 14 couples to a common, or wiper, switch-terminal 48 of a relay 50. A normally-closed switch-terminal 52 of relay 50 couples to a coil-terminal 54 of relay 50, and a coil-terminal 56 of relay 50 couples to a second node of speaker 18 through connectors 24-26.

Wetness sensor 14 operates like a switch, as discussed below in connection with FIG. 3. Relay 50 represents a conventional relay in which coil-terminals 54-56, between which a coil 58 is coupled, act as a control input which controls the open and closed states of a switch 60, connected between terminals 48 and 52. Specifically, when coil 58 is deactivated, switch 60 supplies continuity between terminals 48 and 52, and when coil 58 is activated, switch 60 breaks continuity between terminals 48 and 52. Coil 58 activates when a DC current flows therethrough. A model 275-240, 5 Vdc relay sold by the Radio Shack Corporation represents one example of a relay suitable for use in connection with the present invention. However, those skilled in the art may easily adapt other relays or controlled switches for use in connection with the present invention.

So long as wetness sensor 14 does not experience urine, or any other electrolyte, sensor 14 is open, switch 60 is closed, coil 58 is deactivated, and a cone 62 of speaker 18 is in a first position. Speaker 18 remains silent. As soon as sensor 14 detects urine, continuity is provided between the two nodes of sensor 14, and current flows from battery 42, through sensor 14, switch 60, coil 58, and speaker 18. This current causes the cone 62 to move to a second position. This current additionally activates coil 58, which causes switch 60 to enter its open state. When switch 60 enters its open state, current stops flowing through speaker 18 and coil 58. When the current stops flowing, cone 62 returns to its first position, and coil 58 deactivates. As coil 58 deactivates, switch 60 again enters its closed state. When switch 60 enters its closed state, current can again flow through switch 60, coil 58, and speaker 18. Consequently cone 62 again moves to its second position.

The above-described oscillation of relay 50 and speaker 18 cause speaker 18 to emit an audible sound. The frequency of this sound is not an important parameter in the present invention so long as it remains well within the audio spectrum. The physical construction parameters of relay 50 dictate this frequency, which is typically well within the audio spectrum for many conventional relays. As discussed above, this audible sound continues until connectors 24-26 are separated.

Figure 3:
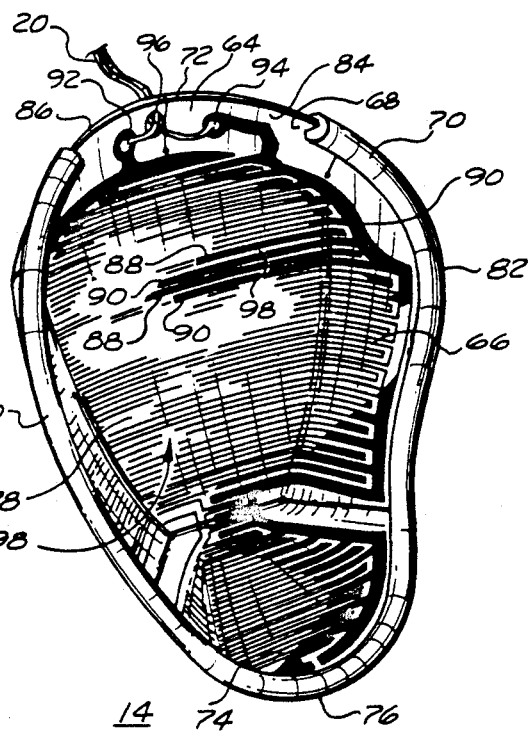
FIG. 3 shows an interior perspective view of a wetness sensor of the present invention.

FIG. 3 shows an interior perspective view of wetness sensor 14. Specifically, sensor 14 includes a substrate 64, a circuit pattern 66 formed on an interior surface 68 of substrate 64, and a resilient pad 70 fitted around an exterior edge 72 of substrate 64. Substrate 64 serves as a wall, which is substantially sealed or otherwise impermeable to fluids, such as urine. Accordingly, substrate 64 repels urine. In addition, substrate 64 is a substantially non-conducting material, and substrate 64 is a flexible material. In addition, substrate 64 is curved to extend in each of three dimensions so that sensor 14 resembles a cup, bowl, or other concave FIGURE. In other words, substrate 64 is a curved wall and not a flat plate. The preferred embodiment utilizes a conventional plastic sheet material which is approximately 0.020–0.050 inches thick and upon which copper is conventionally clad for substrate 64.

Moreover, exterior edge 72 of substrate 64 is shaped to conform to urogenital area 28 (see FIG. 1) of human male anatomy. Specially, a lower region 74 of substrate 64 is curved to fit under the scrotum (not shown). Lower region 74 terminates at a first edge section 76 of exterior edge 72, which is generally curved around a radius located frontwardly external to wearer 12 (see FIG. 1) so that it conforms to the general shape of the genito-urinary region of the perineum (not shown). A mid-region 78 of substrate 64 angles or curves from lower region 74 generally toward the wearer's head in front of his scrotum and penis, and back toward the wearer's body. Mid region 78 terminates at second and third edge sections 80 and 82, respectively, of exterior edge 72. Each of second and third edge sections 80–82 is shaped to conform to the general shape of male anatomy which resides alongside the penis and scrotum between the genito-urinary region of the perineum and the lower region of the abdomen, in the region of the pubes. An upper region 84 of substrate 64 is shaped to angle or curve back toward the wearer's body from the side of mid-region 78 which opposes lower region 74. Upper region 84 terminates at a fourth edge section 86 of exterior edge 72, which is curved to conform to the general shape of the pubes region of the lower abdomen.

Resilient pad 70 completely surrounds substrate 64 at exterior edge 72. Pad 70 is preferably a soft, spongy material which either directly repels urine or is otherwise coated or covered to repel urine. In the preferred embodiment, pad 70 exhibits a cylindrical shape, ½–1 inch in diameter, and is axially slit (not shown) so that exterior edge 72 fits within the slit. Preferably, pad 70 is not permanently attached to substrate 64 so that it may be removed for cleaning purposes, then reinstalled.

Pad 70 simultaneously serves two purposes in the preferred embodiment of the present invention. First, pad 70 conforms and seals substrate 64 to the wearer's body. Consequently, when the wearer urinates, the urine tends to remain between substrate 64 and the wearer's body. Clothing and bedding tend to remain dry. Second, pad 70 enhances the comfort of wearing training aid 10. Accordingly, wearer 12 is motivated to continuously and faithfully wear aid 10 while sleeping.

Circuit pattern 66 formed on interior surface 68 of substrate 64 represents a printed circuit which is geometrically adapted for use in connection with the present invention. Specifically, pattern 66 includes first and second sets of exposed conductive fingers 88 and 90, respectively. Each of sets 88 and 90 has a multiplicity of conductors which resemble fingers. First set 88 couples to a node 92, and second set 90 couples to a node 94. A hole 96 in substrate 64 permits cable 20 to be routed from outside wetness sensor 14 for attachment at nodes 92–94. In addition, pattern 66 includes a sensing area 98, over which conductive finger sets 88–90 are absent. In other words, sensing area 98 spaces finger set 88 apart from finger set 90. Thus, no continuity exists between finger set 88 and finger set 90, absent some external connector, such as an electrolyte like urine, which bridges sensing area 98.

Finger sets 88–90 are interleaved so that they reside along side but spaced apart from one another for a considerable linear distance throughout circuit pattern 66. Preferably, greater than 80 inches, and more preferably greater than 160 inches, of linear distance exists in circuit pattern 66 over which an external connector, such as urine, can electrically couple finger sets 88–90 together. This distance is referred to as the along-side distance below. In addition, sensing area 98 is dimensioned so that a distance of less than 0.100 inch, and more preferably less than 0.030 inch, on average separates finger set 88 from finger set 90 throughout circuit pattern 66. As the separation distance decreases or the along-side distance increases, the chances of a given small quantity of urine activating wetness sensor 14 increase. Thus, circuit pattern 66 maintains the separation distance at a minimum and the along-side distance at a maximum, within practical low-cost printed circuit formation technique constraints. Moreover, circuit pattern 66 resides over at least a majority, and more preferably substantially the entirety, of interior surface 68 of substrate 64.

When wearer 12 (see FIG. 1) initially begins to urinate, only a small quantity of urine discharges. Since the present invention refrains from incorporating any substantial wicking or urine-absorbing material, this entire small quantity of urine collects at some section, depending on the wearer's orientation, of interior surface 68 of substrate 64. Circuit pattern 66, due to the minimized separation distance between finger sets 88–90, the maximized along-side distance between finger sets 88–90, and the large surface area occupied, activates when it encounters this small quantity of urine. As a result of the activation, wetness sensor 14 conducts current, as discussed above in connection with FIG. 2, and the alarm signal is broadcast upon the initiation of urination.

Figure 4:
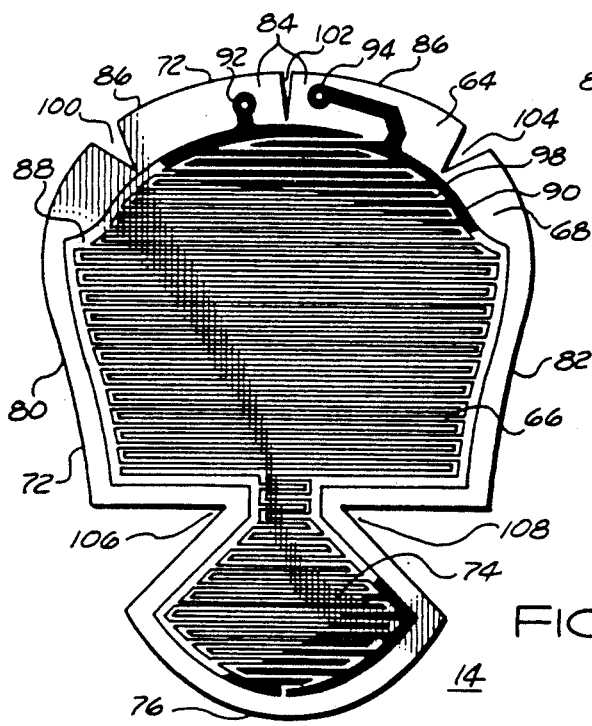
FIG. 4 shows a top, interior view of the wetness sensor portion of the present invention prior to final assembly.

FIG. 4 shows a top, interior view of wetness sensor 14 prior to forming substrate 64 into the shape discussed above in connection with FIG. 3. Conventional two-dimensional printed circuit etching techniques are utilized to form circuit pattern 66 on interior surface 68 of substrate 64. Next, exterior edge 72 is shaped by removing excess portions of substrate 64. Preferably, a line or other marks (not shown) etched on substrate 64 show where to cut substrate 64 so that the desired shape results. Generally speaking, exterior edge 72 is spaced approximately ¼ to ¾ inches outside of the exterior portion of circuit pattern 66.

Next, slots 100, 102, and 104 are cut from fourth edge section 86 inward toward circuit pattern 66 and stopping short of pattern 66. Slot 100 is located approximately ¼ the distance from second edge section 80 to third edge section 82 along fourth edge section 86. Slot 102 is located approximately ½ the distance from second edge section 80 to third edge section 82 along fourth edge section 86, and slot 104 is located approximately ¾ the distance from second edge section 80 to third edge section 82 along fourth edge section 86. In addition, side slots 106 and 108 have been previously cut in substrate 64 by the exterior edge shaping task, discussed above. Side slot 106 resides beneath second edge section 80, and side slot 108 resides beneath third edge section 82.

Substrate 64 is next formed into the three-dimensional shape shown in FIG. 3. This formation is achieved by overlapping substrate 64 a small distance on itself at opposing sides of each of slots 100-108 and applying a suitable adhesive between the overlapped sections of substrate 64. The adhesive is applied so that a liquid-tight bond results. As a result, substrate 64 exhibits a cup-like shape with circuit pattern 66 located on the interior of the cup.

In summary, the present invention provides an improved enuresis avoidance training aid. The present invention tends to keep clothing and bedding from becoming soaked with urine due to the three-dimensional shape of wetness sensor 14 which also conforms to the anatomy of the wearer. The present invention is easily cleaned because it utilizes components which repel urine. Thus, the present invention may be easily and adequately cleaned in a bathroom sink in preparation for subsequent use. The present invention also quickly detects small amounts of urine due to the absence of urine absorbing materials and the optimized circuit pattern formed on interior surface 68 of substrate 64. As a consequence, an alarm is sounded instantly after the wearer begins to urinate. The cup-like shape of substrate 64 and the conformal, pad-covered character of exterior edge 72 enhance the comfort of training aid 10 for the wearer. Furthermore, the adaptability of training aid 10 to conventional clothing garments, the lack of disposable components, and the simplicity of electrical circuit design all contribute to making the present invention inexpensive to purchase and use.

The present invention has been described above with reference to a preferred embodiment. However, those skilled in the art will recognize that changes and modifications may be made in this preferred embodiment without departing from the scope of the present invention. For example, the curved wall of wetness sensor 14 may be achieved using either arc-like geometries or flat plates adjoined at angles. In addition, nothing prevents the installation of an additional urine-absorbing material within wetness sensor 14 for aesthetic purposes, even though the speed with which an alarm sounds may decrease as the quantity of this material increases. The present invention may be constructed in various sizes to accommodate various sizes of wearers. Furthermore, while the above-described embodiment has been especially adapted for the male anatomy, those skilled in the art may devise a similar training aid adapted to the female anatomy. These and other changes and modifications which are obvious to those skilled in the art are intended to be included within the scope of the present invention.

What is claimed is:

1. An apparatus for detecting urine discharged from a body of a wearer, said apparatus comprising:
a wetness sensor having a non-conductive substrate extending in each of three dimensions to form a cup sealable against said body of said wearer so that said urine is substantially retainable between said substrate and said body, said substrate having an interior surface with a circuit pattern formed thereon wherein said circuit pattern extends in each of said three dimensions and includes first and second sets of interleaved conductive fingers; and
means, coupled to said wetness sensor, for emitting an audible signal when said urine is detected.

2. An apparatus as claimed in claim 1 wherein:
said wetness sensor substrate comprises a curved wall having an exterior edge;
said exterior edge of said curved wall includes first, second, third, and fourth edge sections configured in cooperation with human male anatomy so that:
said first edge section conforms to the genera shape of the genito-urinary region of the perineum,
said second edge section conforms to the general shape of the abdomen in the region of the pubes, and
said third and fourth edge sections respectively conform to the general shapes of regions of male anatomy which reside on opposing sides of the penis and scrotum between the pubic region of the abdomen and genito-urinary region of the perineum; and
said curved wall protrudes outward from said exterior edge with respect to said body.

3. An apparatus as claimed in claim 1 wherein said wetness sensor substrate comprises a curved wall having an exterior edge, and said apparatus additionally comprises a resilient pad covering said exterior edge to enhance comfort and sealability of said wetness sensor against said body.

4. An apparatus as claimed in claim 3 wherein said resilient pad is configured to repel said urine.

5. An apparatus as claimed in claim 1 wherein said substrate is configured to repel said urine.

6. An apparatus as claimed in claim 1 wherein said circuit pattern covers a majority of said interior surface of said substrate to permit instant activation of said emitting means upon discharge of said urine.

7. An apparatus as claimed in claim 1 wherein said circuit pattern includes a non-conductive sensing area which spaces said first and second sets of interleaved conductive fingers apart from one another, said sensing area being dimensioned so that a distance between said finger sets averages less than 0.1 inch throughout said circuit pattern.

8. An apparatus as claimed in claim 7 wherein said sensing area is further dimensioned so that said first and second sets of interleaved conductive fingers are spaced said distance apart from a linear distance of more than 80 inches through said circuit pattern.

9. An apparatus as claimed in claim 1 wherein:
said emitting means comprises energizing means, switching means, and a speaker;
said energizing means, said switching means, said speaker, and said wetness sensor are electrically coupled in series with one another; and
said switching means is configured to oscillate between opened and closed states when said urine is detected.

10. An apparatus as claimed in claim 9 wherein:
said switching means comprises a relay having a coil and a switched path formed between a first terminal and a second terminal, said coil and switched path being mutually arranged so that continuity exists between said first and second terminals when said coil is not energized, and continuity does not exist between said first and second terminals when said coil is energized; and
said coil is coupled in series with said switched path.

11. An apparatus as claimed in claim 9 additionally comprising mating plug and socket connector means coupled in series with said energizing means, switching means, and speaker, said plug and socket connector means being mutually configured to separate from one another only after experiencing at least a predetermined separation force.

12. A method of detecting urine discharged from a body, said method comprising the steps of:
   sealing a cup having an interior surface against said body so that said urine is substantially retained between said cup and said body;
   locating a circuit pattern on a majority of said interior surface of said cup to sense the presence of said urine, said circuit pattern having first and second sets of interleaved conductive fingers curved to extend in each of three dimensions and spaced apart by a non-conductive sensing area; and
   emitting an audible alarm sound when said urine is detected by said circuit pattern.

13. A method as claimed in claim 12 additionally comprising the step of providing a pad around said cup to enhance comfort and sealability of said cup against said body.

14. A method as claimed in claim 13 wherein said pad is conformed to repel urine.

15. A method as claimed in claim 12 wherein said cup is formed from a curved wall, and said wall is conformed so as not to absorb urine.

16. A method as claimed in claim 12 wherein said emitting step comprises the steps of:
   activating a control input of a switch when said urine is detected;
   said switch ceasing to conduct current when said control input is activated;
   said control input being deactivated in response to said ceasing to conduct; and
   said switch again conducting current when said control input is de-activated.

17. An apparatus for detecting urine discharged from a human male wearer, said apparatus comprising:
   a non-conductive, urine repelling substrate extending in each of three dimensions and having an interior surface and first, second, third, and fourth sections of an exterior edge, said edge being configured in conformance with the anatomy of said wearer so that:
      said first edge section conforms to the general shape of the genito-urinary region of the perineum,
      said second edge section conforms to the general shape of the abdomen in the region of the pubes, and
      said third and fourth edge sections respectively conform to the general shapes of regions which reside on opposing sides of the penis and scrotum between the pubic region of the abdomen and genito-urinary region of the perineum;
   a resilient pad covering said exterior edge to conformably seal said substrate to said wearer so that said urine is substantially retainable between said substrate and said wearer;
   a circuit pattern formed on said interior surface, said circuit pattern extending in each of said three dimensions, and said circuit pattern having first and second sets of interleaved conductive fingers spaced apart by a nonconductive sensing area; and
   means, coupled to said circuit pattern, for emitting an audible signal when said urine is detected.

18. An apparatus as claimed in claim 17 wherein:
   said emitting means comprises energizing means, switching means, and a speaker;
   said switching means comprises a relay having a coil and a switched path formed between a first terminal and a second terminal, said coil and switched path being mutually arranged so that continuity exists between said first and second terminals when said coil is not energized, and continuity does not exist between said first and second terminals when said coil is energized; and
   said energizing means, coil, switched path, said speaker, and said circuit pattern are electrically coupled in series with one another.

19. An apparatus as claimed in claim 18 wherein said sensing area is dimensioned so that:
   a distance between said first and second conducting finger sets averages less than 0.1 inch throughout said circuit pattern; and
   said first and second sets of interleaved conductive fingers are spaced said distance apart for a linear distance of more than 80 inches through said circuit pattern.

* * * * *

UNITED STATES PATENT AND TRADEMARK OFFICE
CERTIFICATE OF CORRECTION

PATENT NO. : 5,043,704
DATED : August 27, 1991
INVENTOR(S) : William D. Blakeney It is certified that error appears in the above-identified patent and that said Letters Patent is hereby corrected as shown below:

In the Abstract, line 15, change "realy" to --relay--.

In column 8, line 4, change "genera" to --general--.

In column 8, line 41, change "from" to --for--.

Signed and Sealed this

Twenty-ninth Day of September, 1992

*Attest:*

DOUGLAS B. COMER

*Attesting Officer*  *Acting Commissioner of Patents and Trademarks*